(12) United States Patent
Kraenzle

(10) Patent No.: US 7,276,199 B2
(45) Date of Patent: Oct. 2, 2007

(54) MOLDING METHODS INCLUDING MOVABLE CORE PIN SUPPORT

(76) Inventor: David G. Kraenzle, 12845 Big Bend, St. Louis, MI (US) 63122

( * ) Notice: Subject to any disclaimer, the term of this patent is extended or adjusted under 35 U.S.C. 154(b) by 229 days.

(21) Appl. No.: 10/847,038

(22) Filed: May 17, 2004

(65) Prior Publication Data

US 2005/0253301 A1 Nov. 17, 2005

(51) Int. Cl.
*B29C 45/36* (2006.01)
(52) U.S. Cl. .............................. 264/328.7; 264/328.12
(58) Field of Classification Search ............ 264/328.1, 264/328.7, 328.12
See application file for complete search history.

(56) References Cited

U.S. PATENT DOCUMENTS

| | | | | |
|---|---|---|---|---|
| 2,418,823 A | * | 4/1947 | Desimone | 249/94 |
| 2,434,594 A | * | 1/1948 | Schultz | 425/468 |
| 2,822,578 A | * | 2/1958 | Lobell | 249/67 |
| 2,876,495 A | * | 3/1959 | Spillman | 425/567 |
| 3,347,965 A | * | 10/1967 | Valyi | 264/537 |
| 3,509,603 A | * | 5/1970 | Cosme et al. | 425/577 |
| 3,778,211 A | * | 12/1973 | Moen et al. | 425/577 |
| 3,947,203 A | * | 3/1976 | Rose | 264/328.7 |
| 4,050,667 A | * | 9/1977 | Kossett | 425/468 |
| 4,074,434 A | * | 2/1978 | Nielsen et al. | 433/100 |
| 5,165,891 A | * | 11/1992 | Young et al. | 433/95 |
| 5,240,397 A | * | 8/1993 | Fay et al. | 264/328.12 |
| 5,759,647 A | * | 6/1998 | Kuroda et al. | 264/328.7 |
| 6,841,114 B2 | * | 1/2005 | Fujiwara et al. | 264/328.12 |

OTHER PUBLICATIONS

International Search Report from pending application PCT/US2005/15759, 4 pages, mailed Jul. 2006.
Written Opinion from pending application PCT/US2005/15759, 7 pages, mailed Jul. 2006.

* cited by examiner

*Primary Examiner*—Jill L. Heitbrink

(57) ABSTRACT

Apparatus and methods for molding a part with at least one passage at least partially therethrough. Generally, the method includes injecting a molding material into a mold cavity having at least one pin disposed therein to form the passage. In preferred implementations, the injection of molding material can cause displacement of a movable support for the pin and allow molding material to surround the pin to form the passage. Additionally, or alternatively, preferred implementations can include the movable support, when extended into the mold cavity, guiding and ensuring proper alignment of a free end of the pin for capture within a recess defined by at least one portion of the mold. Still yet other preferred implementations can additionally or alternatively include the extended movable support straightening out the pin and/or inhibiting deflection of the pin, which can be caused by the injected molded material.

56 Claims, 8 Drawing Sheets

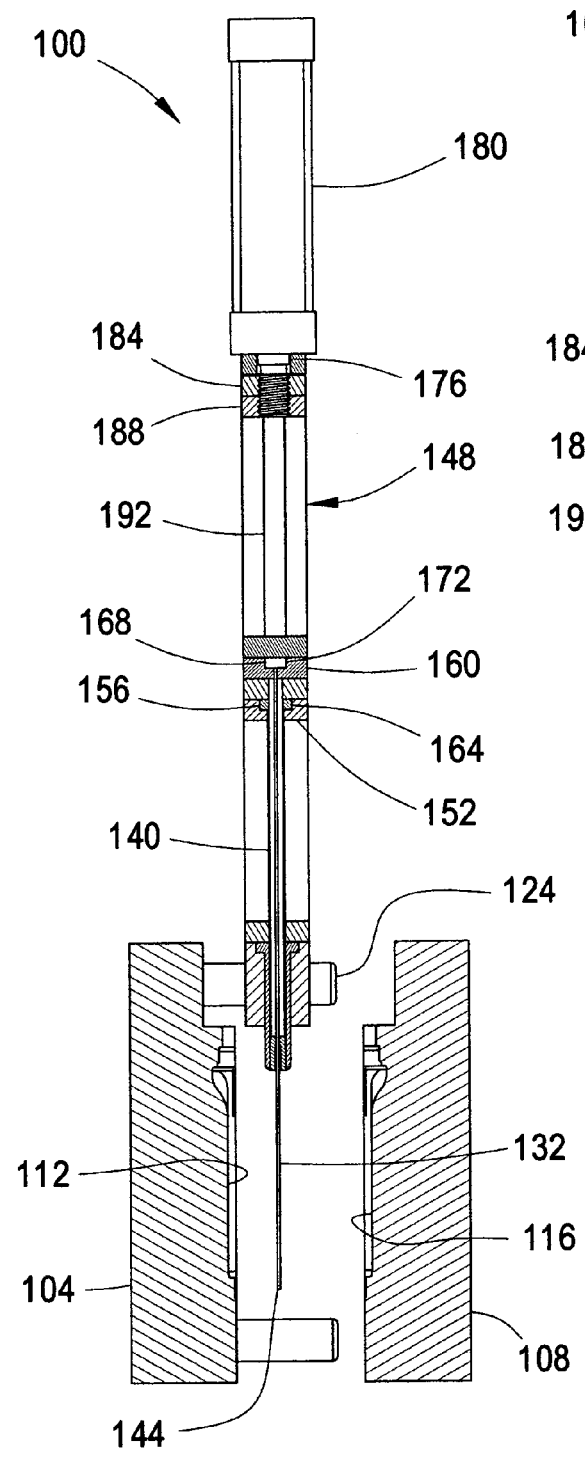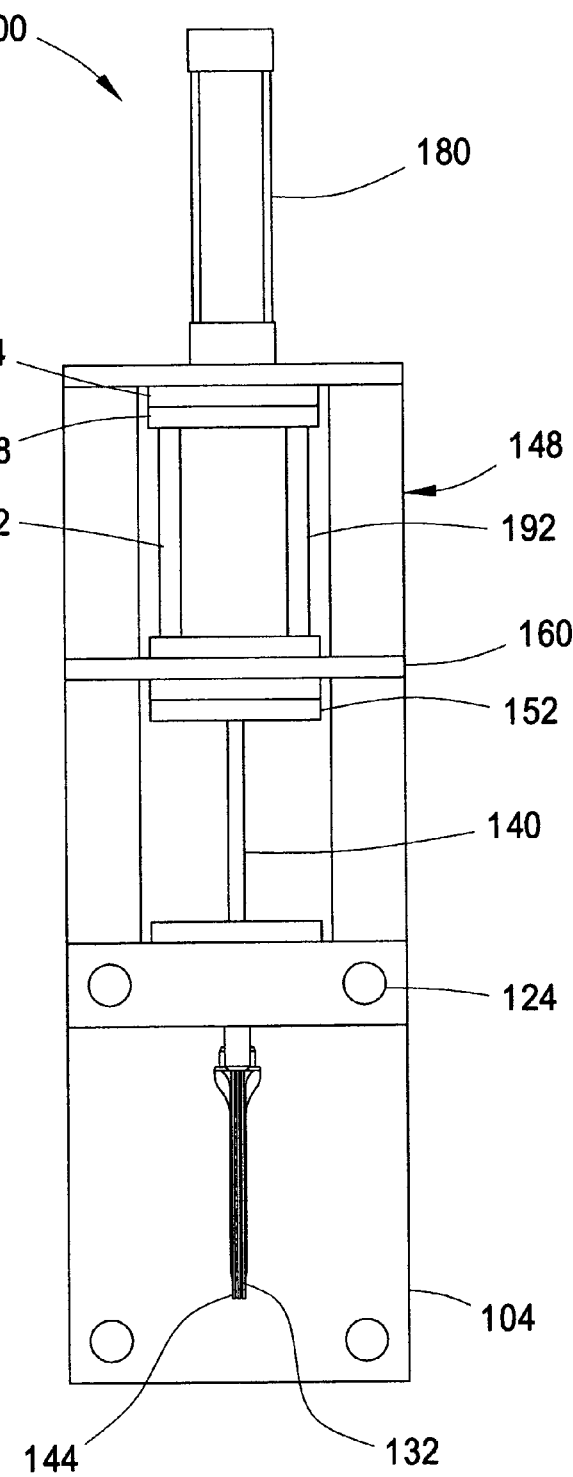

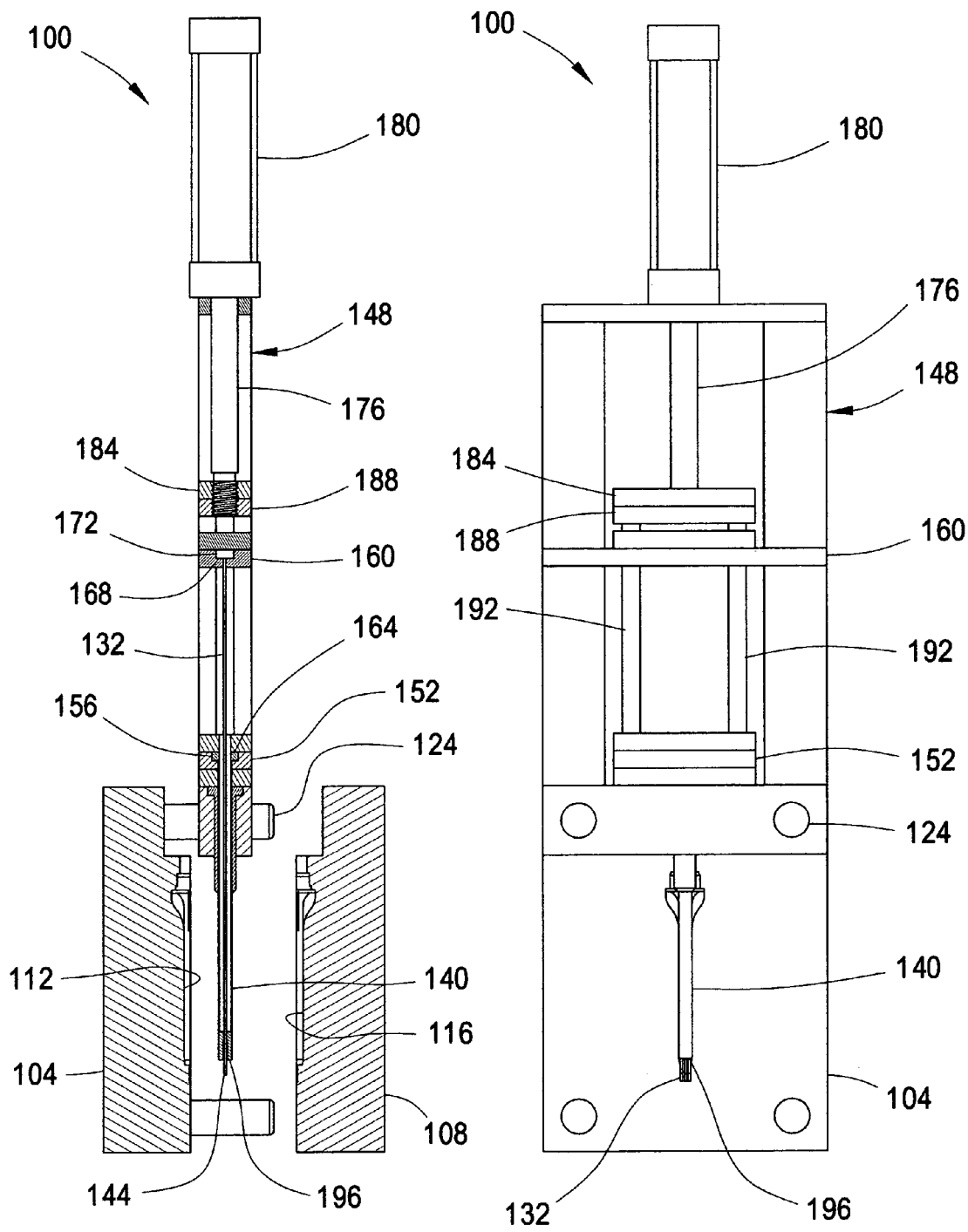

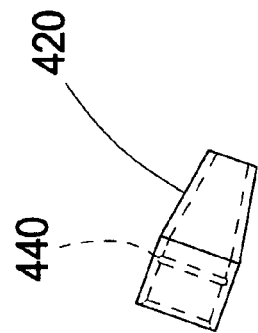
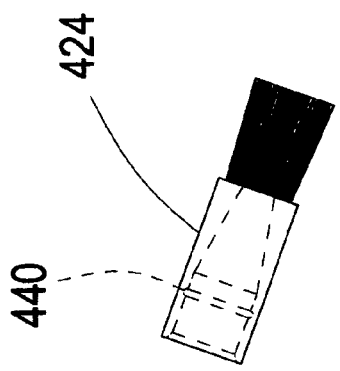
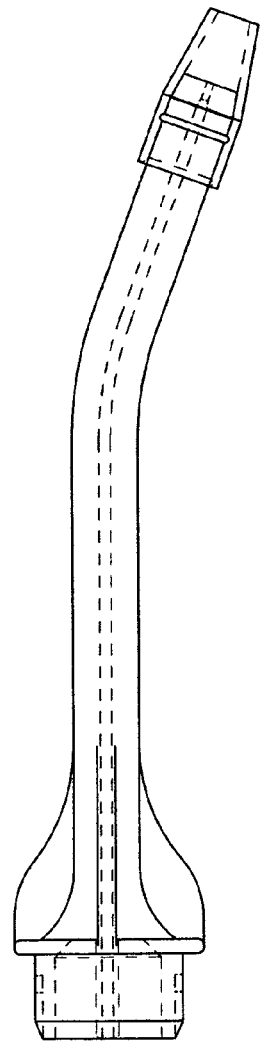
FIG. 11
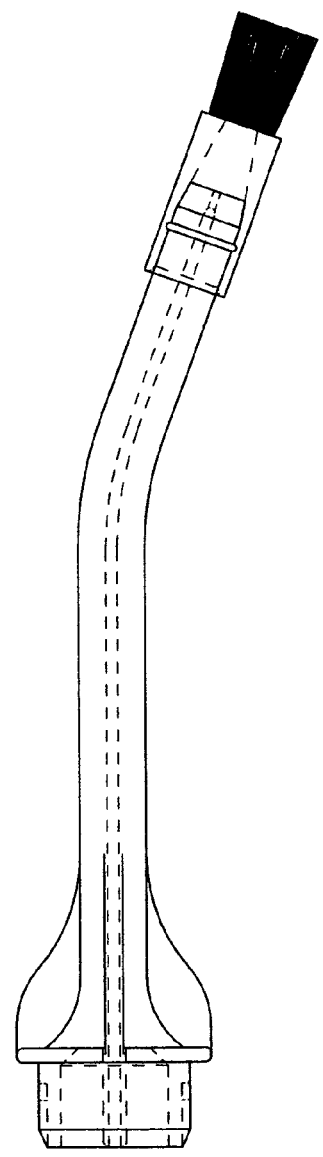
FIG. 12

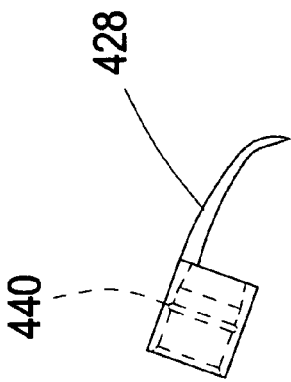
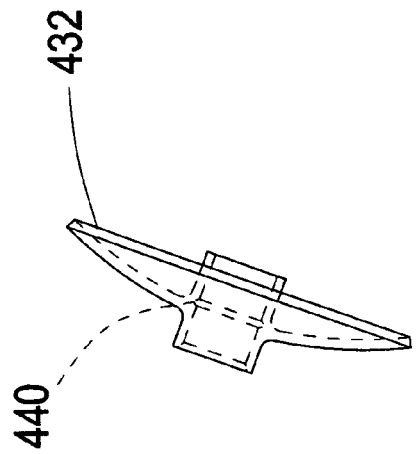
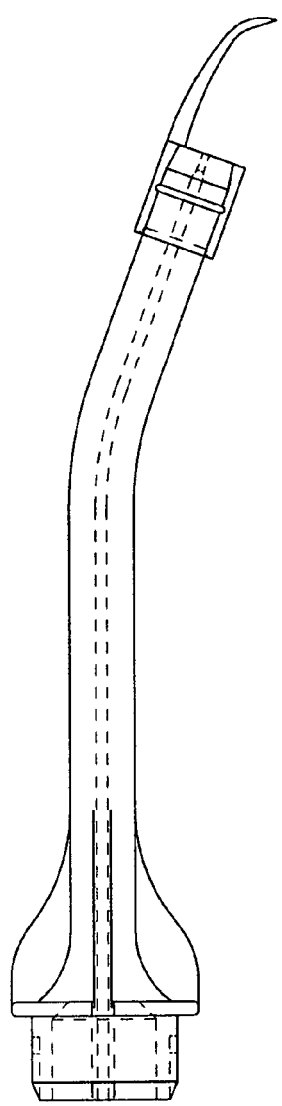
FIG. 13
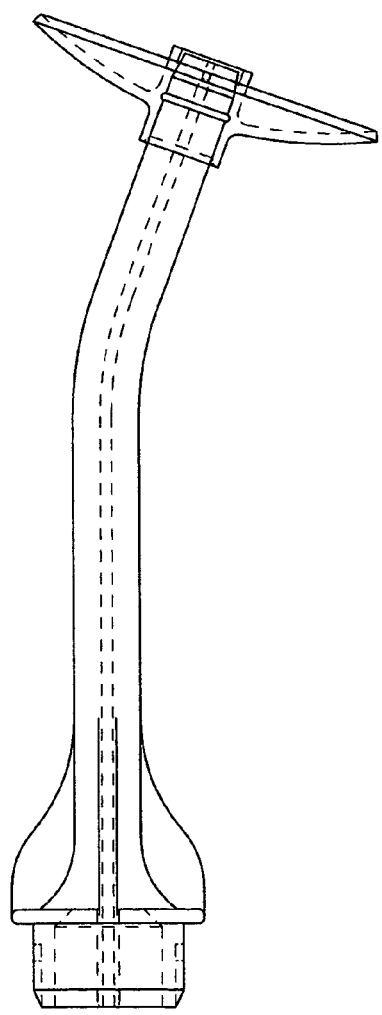
FIG. 14

MOLDING METHODS INCLUDING MOVABLE CORE PIN SUPPORT

FIELD

The present invention relates generally to molding processes. More particularly (but not exclusively), the present invention relates to molding apparatus and methods including a movable core pin support and that can be used to mold parts having passageways at least partially therethough, such as dental syringes commonly used to direct fluids (e.g., air, water, medicated fluids, combinations thereof, etc.) into a patient's oral cavity.

BACKGROUND

Disposable dental tools are becoming more common due at least in part to increased awareness and concern for the spread of infectious diseases, such as hepatitis and AIDS. To remain cost-effective, disposable dental tools must be constructed of inexpensive plastics and manufactured in a relatively inexpensive manner so that they can discarded after use, thus eliminating the expense and inconvenience of sterilization.

Extrusion can produce dental tools and other parts having internal fluid passageways therein. But extrusion can only produce dental tools having a generally uniform cross-section or profile. Post-extrusion processing (e.g., machining, assembling, etc.) is required to add surface features, such as threads and ribs, to the extruded part.

Injection molding can also produce dental tools having internal fluid passages therein. With injection molding, a core pin within the mold cavity is surrounded by molding material that solidifies to form a passageway within the part. To withstand the relatively high pressures at which molding material is injected into the mold cavity, the core pin must have a sufficient moment of inertia relative to its length (e.g., be sufficiently rigid enough) to resist excessive flexing, deflection and/or deformation otherwise caused by the injection pressure.

Accordingly, it can be rather difficult, if not impossible, for existing injection molding systems to mold a part with a relatively small passageway in relation to the length of that passageway. This is because the required core pin would likely have too small of a moment of inertia relative to its length to resist excessive flexing, deflection and/or deformation caused by the injection pressure.

SUMMARY

According to one aspect, the invention provides apparatus and methods for molding a part with at least one passage at least partially therethrough. Generally, the method includes injecting a molding material into a mold cavity having at least one pin disposed therein to form the passage. In preferred implementations, the injection of molding material can cause displacement of a movable support for the pin and allow molding material to surround the pin to form the passage. Additionally, or alternatively, preferred implementations can include the movable support, when extended into the mold cavity, guiding and ensuring proper alignment of a free end of the pin for capture within a recess defined by at least one portion of the mold. Still yet other preferred implementations can additionally or alternatively include the extended movable support straightening out the pin and/or inhibiting deflection of the pin, which can be caused by the injected molded material.

Further areas of applicability of the present invention will become apparent from the detailed description provided hereinafter. It should be understood that the detailed description and specific examples below, while indicating exemplary embodiments of the invention, are intended for purposes of illustration only and are not intended to limit the scope of the invention.

BRIEF DESCRIPTION OF THE DRAWINGS

The present invention will be more fully understood from the detailed description and the accompanying drawings, wherein:

FIG. 1 is a cross-sectional view of an injection molding apparatus including a translatable core pin sleeve shown in a retracted position according to a preferred embodiment of the invention;

FIG. 2 is an elevation view of the injection molding apparatus shown in FIG. 1 with one of the mold halves removed for clarity;

FIG. 3 is a cross-sectional view of the injection molding apparatus shown in FIG. 1 with the sleeve shown in an extended position;

FIG. 4 is an elevation view of the injection molding apparatus shown in FIG. 3 with one of the mold halves removed for clarity;

FIG. 11 is an elevation view of the dental product shown in FIG. 10 with an atomizing tip coupled to the discharge end portion of the dental product;

FIG. 12 is an elevation view of the dental product shown in FIG. 10 with a brush coupled to the discharge end portion of the dental product;

FIG. 13 is an elevation view of the dental product shown in FIG. 10 with a pick coupled to the discharge end portion of the dental product; and FIG. 14 is an elevation view of the dental product shown in FIG. 10 with a shield coupled to the discharge end portion of the dental product.

DETAILED DESCRIPTION OF EXEMPLARY EMBODIMENTS

The following description of preferred embodiments is merely exemplary in nature and is in no way intended to limit the invention, its application, or uses.

FIGS. 1 through 5 illustrate an injection molding apparatus 100 in accordance with the principles of this invention. As shown, the injection molding apparatus 100 includes a corresponding pair of tools or mold halves 104 and 108. It should be noted, however, that molding apparatus 100 can include any suitable number of mold portions (e.g., three, four, etc.) depending on the particular application. Accordingly, the specific references to mold halves herein should not be construed as limiting the scope of the present invention to only molding apparatus having exactly two mold halves or tools.

Figure 5:
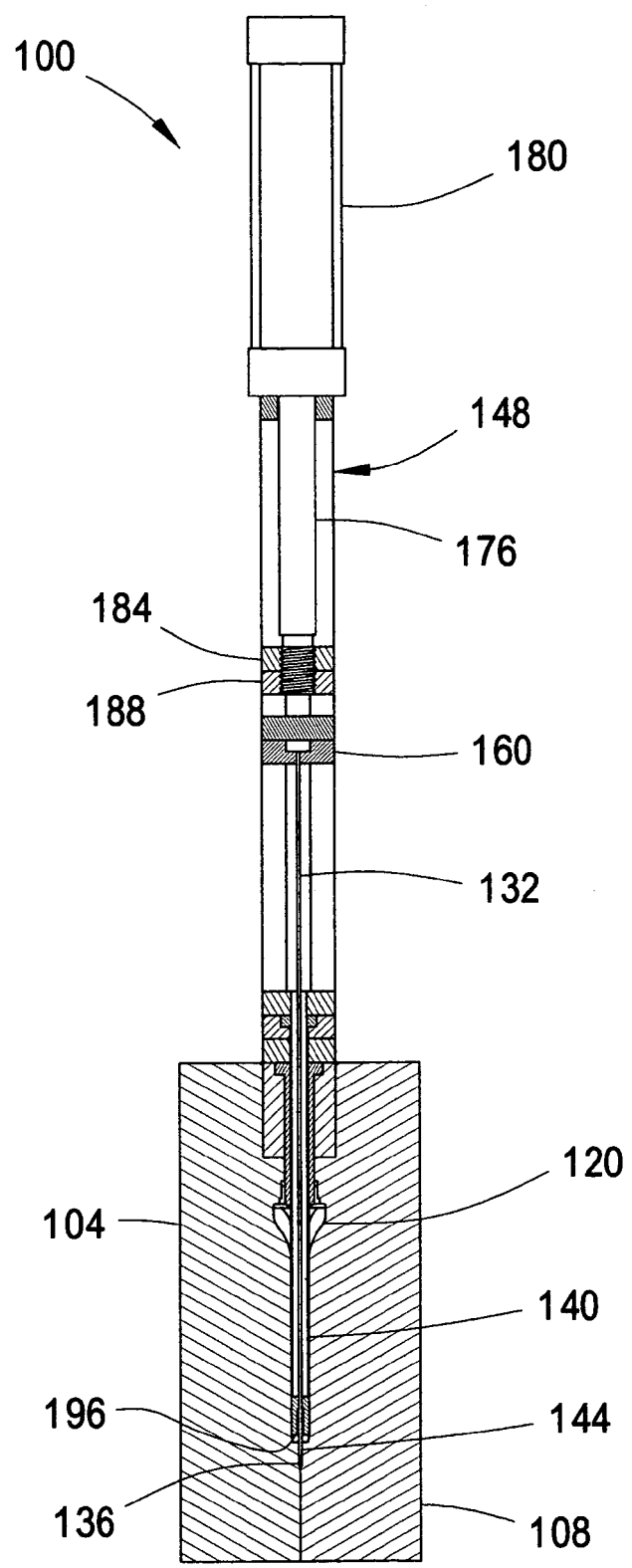
FIG. 5 is a cross-sectional view of the injection molding apparatus shown in FIG. 3 with the mold closed and an end of the core pin captured within a recess defined generally between the closed mold halves.

The mold halves 104 and 108 define corresponding forming surfaces 112 and 116, respectively. As shown in FIG. 5, these surfaces 112 and 116 cooperate to define a mold cavity 120 therebetween when the mold halves 104 and 108 are closed.

While the forming surfaces 112 and 116 are shown configured to produce a dental syringe, it should be noted that forming surfaces 112 and 116 can instead be configured to produce any of a wide range of other parts. It should be further noted that the forming surfaces 112 and 116 can be configured to provide a part with any of a wide range of surface features including ribs, threads, fins, flanges, slots, among other external surface features. By way of example only, another embodiment includes the forming surfaces adapted to produce a pipe or tubing having external threading on each end thereof.

With further reference to FIGS. 1 through 5, the injection molding apparatus 100 can include a plurality of guide pins or rods 124. These rods can assist with the proper alignment of the corresponding mold halves 104 and 108 when they are being closed. In the illustrated embodiment, the injection molding apparatus 100 includes four guide pins 124 coupled to the first mold half 104. The four guide pins 124 are positioned to be received within corresponding holes defined by the second mold half 108 when the first and second mold halves 104 and 108 are properly aligned with one another. Alternatively, other suitable quantities (i.e., one or more) of guide pins and/or other suitable arrangements for the guide pins can be employed.

Opening and closing of the mold halves 104 and 108 can be accomplished in various ways. For example, the first mold half 104 can be moved generally towards or away from the second mold half 108 while the second mold half 108 remains stationary. Alternatively, both mold halves can be moved, and/or the second mold half can be moved while the first mold half remains stationary. Further, a wide range of actuation mechanisms can be used to open and close the mold halves 104 and 108, such as hydraulic actuators, pneumatic actuators, among others.

The injection molding apparatus 100 also includes one or more core pins 132 that extend into the mold cavity 120. During operation of the apparatus 100, molding material injected into the mold cavity 120 can surround the core pins 132 such that the molding material upon solidifying forms a passageway within the part. Depending on the length of the core pins, the core pins can be used to form passageways completely through the finished part and/or passageways or blind holes that extend only partially through the part.

In the illustrated embodiment, the apparatus 100 includes three generally coplanar pins 132. Each pin 132 is sized such that its free end 144 can be captured within a corresponding recess 136 defined generally between the mold halves 104 and 108 when the mold halves 104 and 108 are closed. Each pin 132 includes a generally circular cross-section. With these three core pins 132, the apparatus 100 can produce three generally round, coplanar passageways that extend completely through the part, such as the three passages 204 within the exemplary dental syringe 200 shown in FIG. 6.

Alternatively, other embodiments can include any suitable number of (i.e., one or more) core pins formed from a wide range of suitable materials. In addition, other arrangements, sizes, and cross-sectional shapes (e.g., rectangular, semicircular, triangular, diamond, etc.) can also be employed for the one or more core pins. In those embodiments in which the injection molding apparatus includes more than one core pin, each core pin need not be the same size and/or shape as the other core pins. In addition, the particular number, shape, size, and arrangement of core pin(s) can depend, at least in part, on the particular products being produced and intended purposes for the passage(s) within those products.

The injection molding apparatus 100 also includes a movable support 140 for the core pins 132. As described in more detail below, the movable support is movable relative to the core pins 132 at least between a retracted position (FIGS. 1 and 2) and an extended position (FIG. 3 and 4). When extended, the movable support 140 can guide and ensure proper positioning of each pin's free end 144 for capture within the corresponding recess 136 defined by closing the mold halves 104 and 108. Additionally, or alternatively, the movable support 140 can be configured (e.g., sized, shaped, and/or formed of a sufficiently strong material) to straighten out the pins 132 (as needed) and/or inhibit pin deflection, flexing, and/or deformation, which might otherwise be caused by injection of the molding material. The movable support 140 can also, or instead, be adapted such that injecting molding material into the mold cavity 120 can cause displacement (e.g., retraction, etc.) of the movable support 140.

In the illustrated embodiment, the movable support 140 comprises a single sleeve. The sleeve 140 is adapted to be positioned generally around the core pins 132. As seen by comparing FIGS. 1 and 3, the sleeve 140 is translatable along at least a portion of the length of the pins 132. Alternatively, other implementations can include any suitable number of (i.e., one or more) movable supports or sleeves. For example, other exemplary implementations can include a movable support or sleeve for each core pin. In addition, various implementations can include one or more movable supports that are adapted to be positioned only partially around the core pin(s).

The sleeve 140 can include a generally circular cross-section, although other cross-sectional shapes (e.g., rectangular, semicircular, triangular, diamond, etc.) can be employed. The number, shape, size, and arrangement of the sleeve(s) or movable support(s) can depend, at least in part, on the particular application and products being produced.

The sleeve 140 can be made of one or more various materials capable of withstanding the pressures and temperatures associated with the injection molding process. Further, the sleeve 140 is also preferably formed of one or more materials capable of straightening out the core pins 132, as needed, and/or inhibiting pin deflection, deformation, and/or flexing when the sleeve 140 is extended generally around the core pins 132.

The sleeve 140 can also be configured differently than what is shown in the drawings. In particular, the sleeve 140 does not necessarily have to be slidably movable in a vertical direction. Rather, the movable support could be formed of various other means that are suitable for supporting the core pin(s). For example, various implementations can include offsetting portions of the mold halves themselves that move (e.g., in a generally horizontal direction relative to the figures) into and out of the mold cavity to respectively engage and disengage one or more core pins. These offsetting portions can be caused to extend inwardly into the mold cavity to engage the core pins, for example, by way of a spring-biasing device (e.g., coil spring, etc.), a pressurized source of air (e.g., 180), among other suitable actuation systems (e.g., hydraulic, mechanical, pneumatic, combinations thereof, etc.) These offsetting portions can also be caused to retract out of the mold cavity by injected molding material. By way of further example, various implementations can include a collapsible mold cavity or at least portions thereof that collapse inwardly to support one or more core pin(s) and that can be caused to expand upon injection of molding material into the mold cavity. As another example, various implementations can include a curved sleeve adapted to be slidably positioned about one or more correspondingly curved core pins.

Continuing now with the description of the sleeve 140, a description will now be provided of an exemplary way of movably supporting the sleeve 140 although this can be accomplished in various ways. As shown in FIGS. 1 through 5, the core pins 132 and sleeve 140 can all be supported by a frame 148. The frame 148 can include a movable plate 152 to which the sleeve 140 is coupled, and a stationary plate 160 to which the core pins 132 are coupled.

More specifically, the movable plate 152 can define a counter bore 156 in which a head 164 of the sleeve 140 is positioned. The stationary plate 160 can also define a counter bore 168. This counter bore 168 receives the heads 172 of the core pins 132.

To provide actuation forces for moving the sleeve 140, the apparatus 100 includes a shaft 176 coupled to a pressurized source of air 180 (e.g., an air cylinder, etc.). The shaft 176 is threadedly engaged to plates 184 and 188, which are in turn, coupled to the movable plate 152 by guide pins 192. Accordingly, activating the pressurized source of air 180 causes the shaft 176 to extend downwardly, which, in turn, moves the plates 184 and 188 and guide pins 192 downward. The downward movement of the guide pins 192 cause downward movement of the plate 152 and sleeve 140 coupled thereto. In this exemplary manner, the sleeve 140 can be slidably extended downward along at least a portion of the length of the core pins 132. Alternatively, other suitable actuation devices and methods can be employed to slidably move the sleeve relative to the core pins.

In various implementations, injecting molding material into the mold cavity 120 can cause the sleeve 140 to retract. This sleeve retraction allows molding material to surround the core pins 132 and form passages in the part. Additionally, or alternatively, other means for retracting the sleeve can be employed, for example, to retract the sleeve prior to injecting molding material into the mold cavity. This other means for retracting the sleeve can operate independent from the injected molding material. Alternatively, this other means can operate in conjunction with and assist the injected molding material in causing the sleeve retraction. By way of example only, a spring-biasing device (e.g., coil spring, etc.) can be used to resiliently bias and cause retraction of the sleeve 140.

A description of an exemplary operation of the injection molding apparatus 100 will now be provided. Initially, the pressurized source of air 180 can be activated to extend the shaft 176. This shaft extension causes the plates 152, 184, and 188 and guide pins 192 to move downward. This, in turn, causes the sleeve 140 to extend downwardly into the mold cavity 120 and generally around the core pins 132. As the sleeve 140 translates downwardly along the length of the core pins 132, the sleeve 140 can straighten out the core pins 132.

With the sleeve 140 preferably in a fully extended position, the mold can be closed, which in the illustrated implementation includes moving the first mold half 104 towards the second mold half 108. As the mold is being closed, each core pin free end 144 can be captured within its corresponding recess 136 defined generally between the mold halves 104 and 108. By maintaining the sleeve 140 in the extended position as the mold is closed, the sleeve 140 can ensure that the pin's free ends 144 are properly aligned with their corresponding recesses 136. It should be noted, however, that other implementations can include one or more core pins that are not captured by recesses but instead are surrounded and/or captured by molding material, thereby forming passages or blind holes that extend only partially through the part.

After closing of the mold, a wide range of suitable molding materials can be injected into the cavity 120 via an inlet positioned adjacent the recesses 136 in which the core pins are captured. Alternatively, molding material can be injected into the mold cavity at other suitable locations depending at least in part on the particular application and parts being produced. It should be noted that molding material should not be injected into the mold cavity 120 at a location that would hinder or restrict the movement of the sleeve 140. Preferably, molding material is injected into the mold cavity 120 at a location that assists the retraction of the sleeve 140.

As molding material is injected into the cavity 120, the sleeve 140 is retracted to expose the core pins 132 to molding material. This sleeve retraction allows molding material to flow generally around the core pins 132 and form passages in the part. In a preferred implementation, the sleeve retraction is caused by molding material contacting and applying a sufficient force to the sleeve's free end 196.

To accommodate the sleeve retraction, the pressurized source of air 180 may have to be deactivated. But the pressurized source of air 180 might also be regulated, for example, to provide optional back pressure to the sleeve 140.

In various implementations, the sleeve 140 can be maintained in an at least partially extended position to allow the sleeve 140 to help stabilize and inhibit deflection of the core pins 132 as molding material is injected into the mold cavity 120. Or, for example, the sleeve 140 might remain at least partially extended into the cavity 120 to allow molding material to flow generally around the sleeve 140 and form a recess, such as a countersink or a counterbore in the molded part.

Upon sufficient solidification of the molding material within the mold cavity 120, the mold can be opened, which in the illustrated implementation includes moving the first mold half 104 away from the second mold half 108. At which point, the pressurized source of air 180 can be activated to extend the sleeve 140. When being extended, the sleeve 140 can contact the part on the core pins 132 to eject or strip the part from the core pins 132. Alternatively, other suitable devices and methods can be employed for ejecting or stripping the part from the core pin(s), such as robotic arms or picker devices.

After the part is removed from the mold cavity 120, the part may undergo further post-molding processing depending on the particular application. For example, FIGS. 7, 9, and 10-14 illustrate various dental syringes 200, 300, and 400 that underwent post-molding processing to bend a discharge end portion of the dental syringe.

Accordingly, various implementations of the invention can advantageously be used with relatively long core pins because the movable support can locate and guide even these longer pins for capture within corresponding recesses defined by a mold. Further, various implementations can be used with less rigid core pins and/or core pins having relatively small moments of inertia because the movable support (e.g., sleeve) can support, straighten out, and/or inhibit deflection of these core pins. Indeed, the movable support (e.g., sleeve) can enable the use of core pins of virtually any configuration (e.g., moment of inertia, size, length, width, cross-sectional shape, aspect ratio, etc.) and the molding of parts with passages having virtually any corresponding configuration.

While extrusion can be used to form parts having internal passageways completely therethrough, extrusion can only produce parts having a generally uniform cross-section or profile. Post-extrusion processing (e.g., machining, assembling, etc.) is required to add external surface features, like threads and ribs, to the extruded product. On the other hand, implementations of the present invention can be used to mold products having passageways therein and surface features (e.g., threads, fins, flanges, ribs, etc.) without requiring additional post-molding processes to provide such surface features. Because they can be integrally molded as a single component, monolithically or unitarily constructed parts produced in accordance with the principles of the present invention can include exceptionally consistent positioning and orientation of the various part components relative to one another.

While aspects of the invention are applicable for molding a wide range of products, various implementations include molding dental syringes (some of which are described below). Indeed, various implementations of the present invention have the flexibility to mold dental syringes having any number of (i.e., one or more) passageways in various shapes, sizes, and arrangements which are suitable for a great number of different applications. The particular number, shape, size, and arrangement of passageways will likely depend on the particular application intended for the dental syringe, the particular type of handpiece to which the dental syringe will be connected, and the intended uses for the dental syringe's passageway(s). Exemplary uses for such passageways include directing fluids (e.g., water, air, medicated fluids, anesthetics, mouthwash, combinations thereof, etc.) into a patient's oral cavity. As another example, one or more passageways can receive optical fibers therein which conduct light into the patient's oral cavity. Additionally, or alternatively, various implementations can include molding dental syringes out of one or more suitable materials that enable the dental syringes themselves (without the need for optical fibers therein) to conduct light from a light source into the patient's oral cavity.

Figure 6:
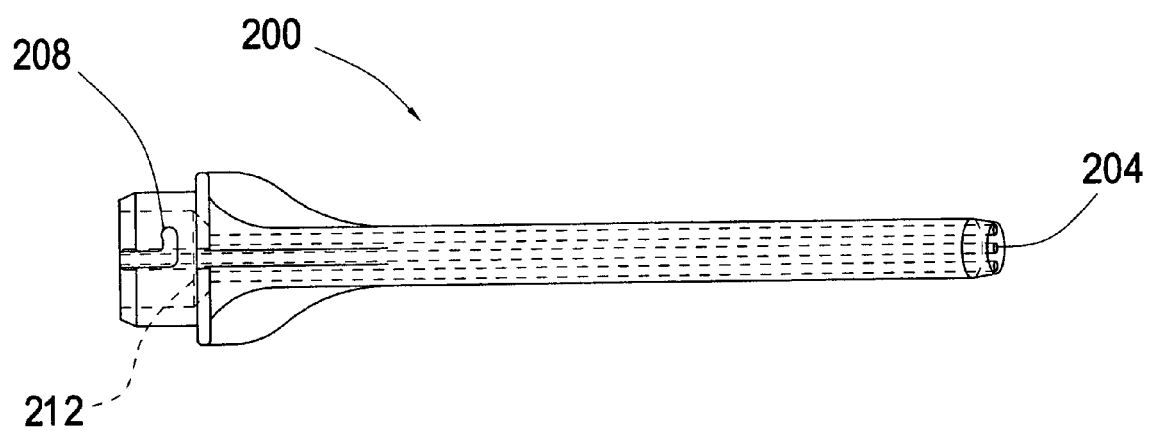
FIG. 6 is an elevation view of an exemplary dental product that can be injection molded in accordance with the principles of the present invention.

FIG. 6 illustrates an exemplary dental syringe 200 that can be produced in accordance with the principles of the present invention. As shown, the dental syringe 204 includes three internal passages 204 and a plurality of generally L-shaped slots 208. The dental syringe 200 and components thereof, e.g., passages 204 and slots 208, can be preferably formed by injection molding without requiring any additional post-molding processes to produce the passages 204 or slots 208.

Each slot 208 can be sized to receive a corresponding locking member defined by a dental handpiece (not shown). Alternatively, a wide range of other suitable fastening features (e.g., internal and/or external threads, ribs, detents, recesses, slots, locking fingers, etc.) can be provided to the dental syringe to enable the dental syringe to be releasably coupled to the dental handpiece.

Figure 7:
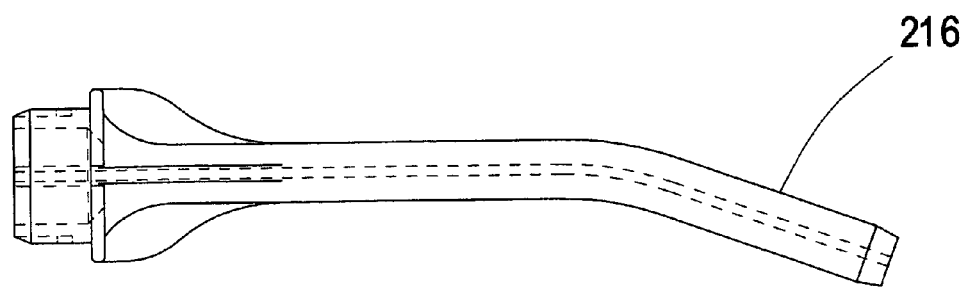
FIG. 7 is a top view of the dental product shown in FIG. 6 and illustrating the bent discharge end portion of the dental product.

As shown in FIG. 7, the discharge end portion 216 of dental syringe 200 is bent to an appropriate angle (e.g., about 30 degrees, etc.). The bending of the discharge end portion 216 can occur after the molding process used to produce the dental syringe 200 is completed. The bent portion 216 of the syringe 200 can provide easier access and more ergonomic aiming of the syringe 200 while being used to dispense fluids into a patient's oral cavity.

Figure 8:
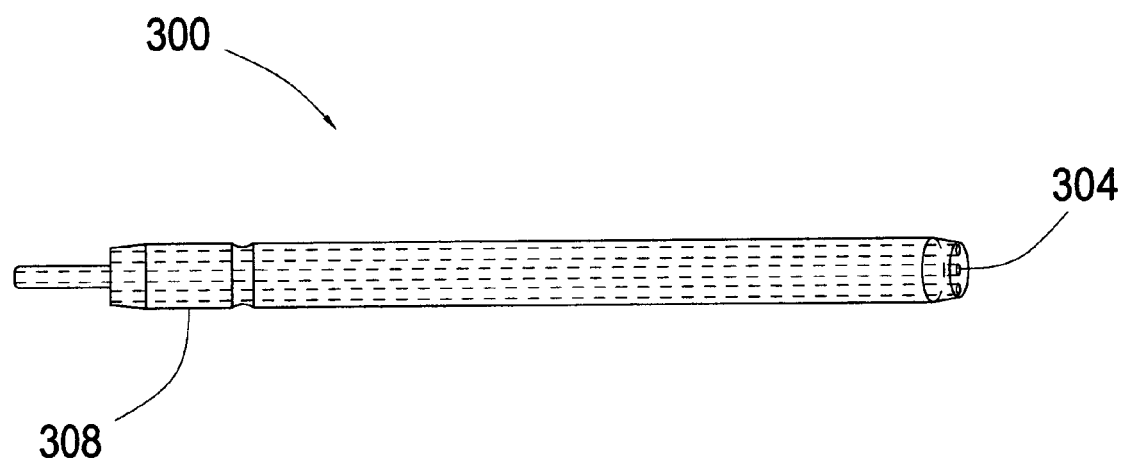
FIG. 8 is an elevation view of an exemplary dental product that can be injection molded in accordance with the principles of the present invention.

FIG. 8 illustrates another exemplary dental syringe 300 that can be produced in accordance with the principles of the present invention. As shown, the dental syringe 300 includes three internal passages 304. The dental syringe 300 also includes a concentric tube attachment feature 308 for connecting the dental syringe 300 to a dental handpiece. Again, however, a wide range of other suitable fastening features (e.g., threads, etc.) can be employed to enable the dental syringe to be coupled to the dental handpiece.

Figure 9:
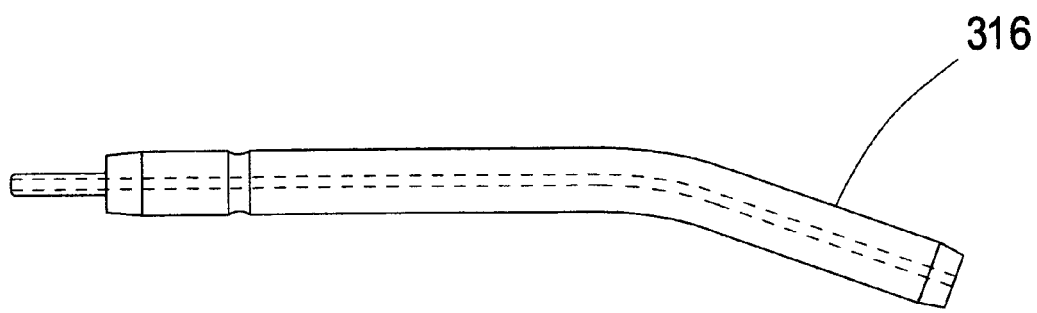
FIG. 9 is a top view of the dental product shown in FIG. 8 and illustrating the bent discharge end portion of the dental product.

As shown in FIG. 9, the discharge end portion 316 of dental syringe 300 has been bent to an appropriate angle (e.g., about 30 degrees, etc.). The bending of the discharge end portion 316 can occur after completion of the molding process used to produce the dental syringe 300.

Figure 10:
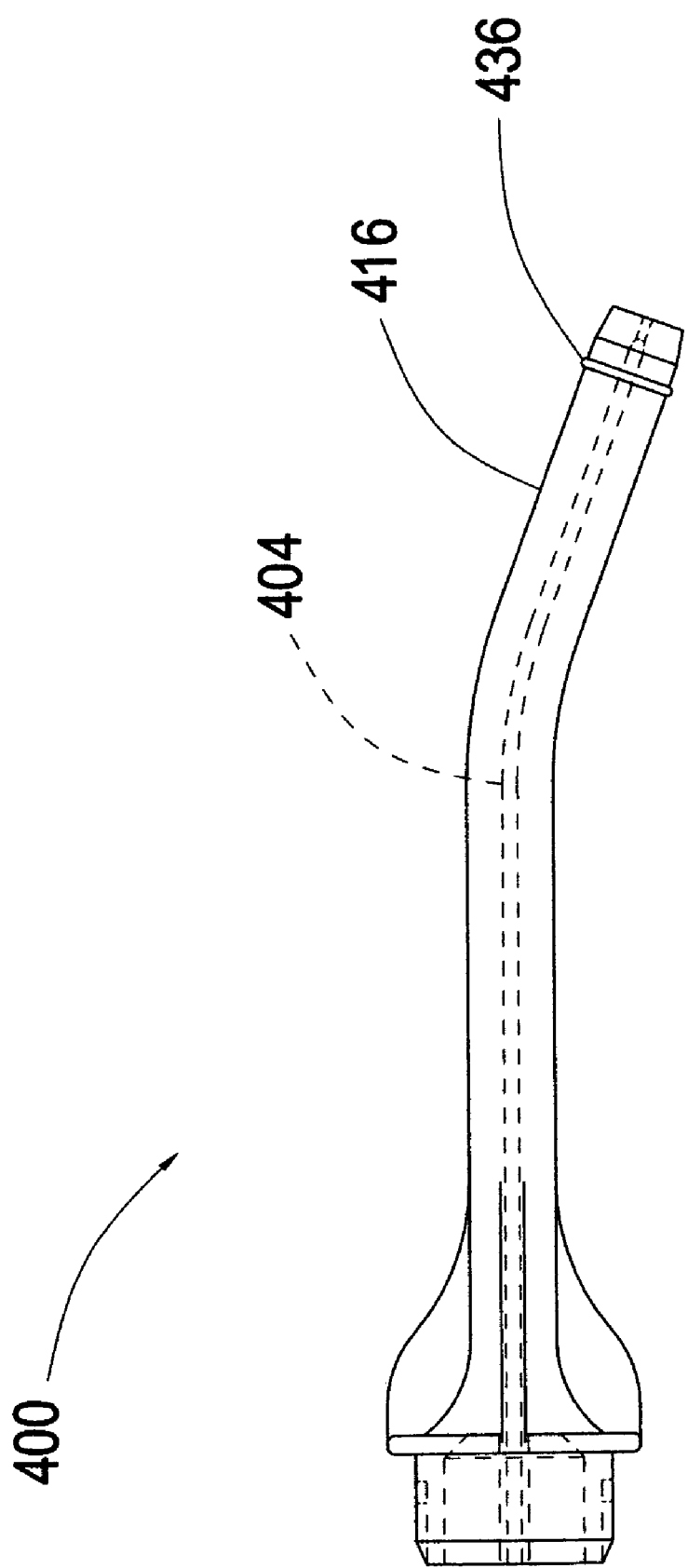
FIG. 10 is an elevation view of an exemplary dental product that can be injection molded in accordance with the principles of the present invention and that includes a discharge end portion adapted to couple with any one of a plurality of interchangeable dental tip devices.

FIG. 10 illustrates another exemplary dental syringe 400 in accordance with the principles of the present invention. As shown, the dental syringe 400 includes one or more internal passages 404. The dental syringe 400 can also include a wide range of suitable fastening means (e.g., threads, ribs, etc.) to enable the dental syringe 400 to be coupled to a dental handpiece.

The dental syringe 400 includes a discharge end portion 416 adapted to couple with any one of a plurality of interchangeable dental tip devices. The tip devices can have a variety of sizes and configurations, to allow the dental syringe 400 to be customized for a particular application or purpose. By selecting and installing the tip device having the most suitable size and configuration for a particular task, operation of the dental syringe 400 can be even further improved. Exemplary tip devices include an atomizing tip 420 (FIG. 11), a brush 424 (FIG. 12), a pick 428 (FIG. 13), and a shield 432 (FIG. 14).

In the illustrated embodiment, the dental syringe 400 includes a resilient rib 436 disposed generally around the syringe 400 adjacent the discharge end portion 416. The dental syringe 400 and its components, e.g., passage 404 and rib 436, can be formed by injection molding in accordance with the principles of the present invention.

As shown in FIGS. 11 through 14, the rib 436 can be sized to fit within any one of the grooves 440 defined by each of the tip devices 420, 424, 428, 432. Engagement of the rib 436 with the groove 440 can form an interference or friction fit between the dental syringe 400 and the corresponding tip device.

Alternatively, a wide range of other suitable fastening systems and methods (e.g., threads, etc.) can be employed to enable the dental syringe to be releasably coupled to any one of a plurality of interchangeable tip devices.

While preferred implementations have been described in relation to injection molding processes, aspects of the invention are also applicable to other molding processes including compression molding, reaction injection molding (RIM), resin transfer molding (RTM), among others.

In addition, aspects of the invention are applicable for molding a wide range of variously sized parts having any suitable number of (i.e., one or more) internal passageways or blind holes. Accordingly, the specific references to dental products, tools, and syringes herein should not be construed as limiting the scope of the present invention to molding any one specific form/type of part.

The description of the invention is merely exemplary in nature and is in no way intended to limit the invention, its application, or uses. Thus, variations that do not depart from the substance of the invention are intended to be within the scope of the invention. Such variations are not to be regarded as a departure from the spirit and scope of the invention.

What is claimed:

1. A method of molding a part with at least one passage completely therethrough, the method comprising:
    extending a movable support through a portion of a mold body into a mold cavity defined by at least two opposing mold portions of a mold along at least a portion of at least one pin as the pin remains stationary relative to the mold cavity, to guide a free end of the pin for capture within a recess cooperatively defined by the at least two opposing mold portions adjacent the mold cavity, the pin being disposed within the mold cavity for forming the passage; and
    injecting molding material into the mold cavity as the pin's free end is captured within the recess and securely retained therein by the mold throughout the complete entirety of the injecting of molding material.

2. The method of claim 1, further comprising closing the at least two opposing mold portions of the mold to capture the free end of the pin within the recess.

3. The method of claim 1, wherein the injecting of molding material causes displacement of the movable support and wherein the method includes allowing molding material to surround the pin to form the passage.

4. The method of claim 1, further comprising at least partially retracting the movable support as molding material is being injected into the mold cavity.

5. The method of claim 1, further comprising at least partially retracting the movable support prior to injecting molding material into the mold cavity.

6. The method of claim 1, wherein the movable support is translatable along at least a portion of the length of the pin.

7. The method of claim 1, further comprising maintaining the movable support in a partially extended position as molding material is being injected into the mold cavity such that the molding material surrounds the pin and at least a portion of the movable support to form a recess within the molded part.

8. The method of claim 1, further comprising removing a molded part from the pin by extending the movable support.

9. The method of claim 1, wherein the at least one pin includes a plurality of pins disposed within the mold cavity for forming a part having a plurality of passages therethough.

10. The method of claim 9, wherein the mold defines a plurality of recesses each sized to capture a free end of a corresponding one of the plurality of pins, and wherein the movable support, when extended into the mold cavity, guides the free end of each said pin for capture within a corresponding recess defined by at least one portion of the mold.

11. The method of claim 1, wherein the part comprises a dental syringe.

12. The method of claim 11, wherein the dental syringe includes a discharge end portion adapted to removably couple with any one of a plurality of interchangeable tip devices.

13. The method of claim 1, wherein the movable support, when extended, provides support for at least the lengthwise portion of the pin along which the movable support has been extended.

14. The method of claim 1, wherein the movable support comprises a tubular sleeve longitudinally slidable over the outer surface of the pin for supporting at least the lengthwise portion of the pin over which the tubular sleeve has been slidably extended.

15. The method of claim 1, wherein molding material is injected into the mold cavity at a location between the captured free end of the pin and the free end of the movable support such that the injected molded material assists retraction of the movable support.

16. The method of claim 2, further comprising removing the molded part from the mold by:
    opening the at least two closed opposing mold portions; and
    stripping the molded part from the pin and ejecting the molded part by extending the movable support from a retracted position as the pin remains stationary relative to the mold cavity.

17. A method of molding a part with at least one passage completely therethrough, the method comprising:
    extending a movable support through a portion of a mold body into a mold cavity defined by at least two opposing mold portions, longitudinally along at least a portion of the length of at least one pin disposed within and remaining stationary relative to the mold cavity such that the movable support helps align a free end of the pin for capture within a recess cooperatively defined by the at least two opposing mold portions adjacent the mold cavity and such that the movable support provides support for at least the lengthwise portion of the pin along which the movable support has been extended to at least inhibit deflection of the pin;
    capturing the pin's free end within the recess defined by the at least two opposing mold portions of the mold; and
    injecting molding material into the mold cavity as the pin's free end is captured within the recess and securely retained therein by the mold.

18. The method of claim 17, further comprising maintaining the movable support in a partially extended position as molding material is being injected into the mold cavity such that the molding material surrounds at least a portion of the movable support and the pin to form a recess within the molded part.

19. The method of claim 17, further comprising closing the mold to capture the free end of the pin within the recess.

20. The method of claim 17, further comprising injecting molding material into the mold cavity, the injecting causing displacement of the movable support and allowing molding material to surround the pin to form the passage.

21. The method of claim 17, further comprising at least partially retracting the movable support as molding material is being injected into the mold cavity.

22. The method of claim 17, further comprising at least partially retracting the movable support prior to injecting molding material into the mold cavity.

23. The method of claim 17, wherein the movable support is translatable along at least a portion of the length of the pin.

24. The method of claim 17, further comprising removing a molded part from the pin by extending the movable support.

25. The method of claim 17, wherein the at least one pin includes a plurality of pins disposed within the mold cavity for forming a part having a plurality of passages therethough.

26. The method of claim 25, wherein the movable support, when extended into the mold cavity, at least inhibits deflection of each said pin.

27. The method of claim 17, wherein the part comprises a dental syringe.

28. The method of claim 27, wherein the dental syringe includes a discharge end portion adapted to removably couple with any one of a plurality of interchangeable tip devices.

29. The method of claim 17, wherein the pin's free end remains captured within the recess during the entire step of injecting molding material into the mold cavity.

30. The method of claim 17, wherein molding material is injected into the mold cavity at a location between the captured free end of the pin and the free end of the movable support such that the injected molded material assists retraction of the movable support.

31. The method of claim 19, further comprising removing the molded part from the mold by:
opening the at least two closed opposing mold portions; and
stripping the molded part from the pin and ejecting the molded part by extending the movable support from a retracted position as the pin remains stationary relative to the mold cavity.

32. A method of molding a part with at least one passage extending completely therethrough, the method comprising:
sliding a tubular sleeve along at least a lengthwise portion of at least one pin disposed within a mold cavity defined by at least two opposing mold portions of a mold, the tubular sleeve sliding to help align a free end of the pin for capture within a recess cooperatively defined by the at least two opposing mold portions adjacent the mold cavity, the tubular sleeve providing support for at least the lengthwise portion of the pin along which the tubular sleeve has been extended;
capturing the pin's free end within the recess defined cooperatively by and generally between opposing mold portions of the mold by closing the opposing mold portions of the mold; and
injecting molding material into the mold cavity as the pin's free end remains captured within the recess and securely retained therein by the mold throughout the entire injecting of molding material into the mold cavity, the molding material being injected into the mold cavity at a location between the captured free end of the pin and the free end of the tubular sleeve such that the injected molded material assists retraction of the tubular sleeve.

33. The method of claim 32, further comprising removing the molded part from the mold by:
opening the at least two closed opposing mold portions; and
stripping the molded part from the pin and ejecting the molded part by extending the movable support from a retracted position as the pin remains stationary relative to the mold cavity.

34. A method of molding a part with at least one passage extending completely therethrough by using a molding apparatus having a mold cavity cooperatively defined by at least two opposing mold portions, at least one pin disposed within the mold cavity to form the passage, a movable support, and an inlet for injecting molding material into the mold cavity, the method comprising:
sliding the movable support along at least a lengthwise portion of the pin as the pin remains stationary relative to the mold cavity, the movable support sliding to help align a free end of the pin for capture within a recess cooperatively defined by the at least two opposing mold portions when closed, the movable support extending through a portion of the mold body into the mold cavity;
closing the at least two opposing mold portions to capture and securely hold the free end of the pin within the recess cooperatively defined between the at least two closed opposing mold portions; and
injecting molding material into the mold cavity as the pin's free end remains captured within the recess and securely retained therein by the at least two closed opposing mold portions throughout the complete process of injecting molding material into the mold cavity, the movable support providing support for at least a portion of the lengthwise portion of the pin along which the movable support has been positioned.

35. The method of claim 34, wherein the injected molding material assists retraction of the movable support.

36. The method of claim 34, further comprising removing the molded part from the mold by:
opening the at least two closed opposing mold portions; and
stripping the molded part from the pin and ejecting the molded part by extending the movable support from a retracted position as the pin remains stationary relative to the mold cavity.

37. The method of claim 34, wherein the movable support comprises a tubular sleeve longitudinally slidable over the outer surface of the pin for supporting at least a portion of the lengthwise portion of the pin over which the tubular sleeve has been slidably positioned, and wherein the molding apparatus comprises a movable member to which the tubular sleeve is coupled for moving the tubular sleeve relative to the mold cavity and the pin.

38. The method of claim 34, wherein the molded part comprises one or more protrusions along the molded part's external surface.

39. The method of claim 34, wherein the molded part comprises one or more ribs, threads, fins, flanges, grooves, or slots along the molded part's external surface.

40. The method of claim 34, wherein the molded part comprises one or more external surface features.

41. The method of claim 34, wherein the movable support, when extended into the mold cavity, at least inhibits deflection of the pin.

42. The method of claim 34, wherein the movable support is translatable along at least a portion of the length of the pin.

43. The method of claim 34, wherein the injecting causes only partial displacement of the movable support such that the molding material surrounds at least a portion of the movable support and the pin to form a recess within the molded part.

44. The method of claim 34, wherein the at least one pin includes a plurality of pins disposed within the mold cavity for forming a part having a plurality of passages therethough.

45. The method of claim 43, wherein the movable support supports each said pin.

46. The method of claim 34, wherein the part comprises a dental syringe.

47. The method of claim 46, wherein the dental syringe includes a discharge end portion adapted to removably couple with any one of a plurality of interchangeable tip devices.

48. The method of claim 34, wherein the injecting of molding material causes displacement of the movable support, and wherein the method includes allowing molding material to surround the pin to form the passage.

49. The method of claim 34, further comprising at least partially retracting the movable support as molding material is being injected into the mold cavity.

50. The method of claim 34, further comprising at least partially retracting the movable support prior to injecting molding material into the mold cavity.

51. The method of claim 34, wherein the movable support comprises a tubular sleeve longitudinally slidable over the outer surface of the pin for supporting at least the lengthwise portion of the pin over which the tubular sleeve has been slidably extended.

52. The method of claim 51, wherein the tubular sleeve is configured to help straighten the pin when the tubular sleeve is slidably extended longitudinally along the outer surface of the pin.

53. The method of claim 34, wherein the injecting of molding material causes retraction of the movable support.

54. The method of claim 53, wherein the injected molded material contacts a free end of the movable support to thereby cause retraction of the movable support.

55. The method of claim 34, wherein molding material is injected into the mold cavity at a location between the captured free end of the pin and the free end of the movable support such that the injected molded material assists retraction of the movable support.

56. The method of claim 34, wherein the movable support comprises a tubular sleeve longitudinally slidable over the outer surface of the pin for supporting at least a portion of the lengthwise portion of the pin over which the tubular sleeve has been slidably positioned, and wherein the molding apparatus comprises a movable plate, external to the mold cavity to which the tubular sleeve is coupled for moving the tubular sleeve relative to the mold cavity and the pin.

* * * * *